(12) United States Patent
Whitt et al.

(10) Patent No.: US 9,668,662 B2
(45) Date of Patent: *Jun. 6, 2017

(54) METHOD AND DEVICE FOR DETECTING AND ASSESSING REACTIVE HYPEREMIA USING SEGMENTAL PLETHYSMOGRAPHY

(71) Applicant: CORDEX SYSTEMS, LLC, Annapolis, MD (US)

(72) Inventors: Michael David Whitt, South Bend, IN (US); Kathy Elizabeth Magliato, Pacific Palisades, CA (US); Stephen Ritterbush, Great Falls, VA (US)

(73) Assignee: CORDEX SYSTEMS, INC., Annapolis, MD (US)

( * ) Notice: Subject to any disclaimer, the term of this patent is extended or adjusted under 35 U.S.C. 154(b) by 363 days.

This patent is subject to a terminal disclaimer.

(21) Appl. No.: 14/204,678

(22) Filed: Mar. 11, 2014

(65) Prior Publication Data

US 2014/0194754 A1    Jul. 10, 2014

Related U.S. Application Data

(63) Continuation of application No. 12/792,504, filed on Jun. 2, 2010, now Pat. No. 8,708,921.

(Continued)

(51) Int. Cl.
*A61B 5/0295* (2006.01)
*A61B 5/02* (2006.01)
(Continued)

(52) U.S. Cl.
CPC ............ *A61B 5/0295* (2013.01); *A61B 5/022* (2013.01); *A61B 5/02007* (2013.01); *A61B 5/02255* (2013.01)

(58) Field of Classification Search
CPC ... A61B 5/0295; A61B 5/022; A61B 5/02255; A61B 5/02007
See application file for complete search history.

(56) References Cited

U.S. PATENT DOCUMENTS 5,724,981 A    3/1998  Apple
6,309,359 B1   10/2001 Whitt et al.
(Continued)

FOREIGN PATENT DOCUMENTS

JP    06319707 A    11/1994
JP    2001087234 A   4/2001

OTHER PUBLICATIONS

International Search Report and Written Opinion issued in Application No. PCT/US2014/070803 on Apr. 23, 2015.

(Continued)

*Primary Examiner* — Meredith Weare
(74) *Attorney, Agent, or Firm* — Michael Ye; Andrews Kurth Kenyon LLP (57) ABSTRACT

A method for measuring reactive hyperemia in a subject is disclosed. The method includes performing a first segmental cuff plethysmography to generate a baseline arterial compliance curve and/or a baseline pressure-area (P-A) curve, performing a second segmental cuff plethysmography to generate a hyperemic arterial compliance curve and/or a hyperemic P-A curve, and calculating an area between the baseline and the hyperemic curves. The size of the area can be used as an indication of endothelial dysfunction (ED) and ED-related diseases.

8 Claims, 8 Drawing Sheets

Related U.S. Application Data (60) Provisional application No. 61/213,369, filed on Jun. 2, 2009.

(51) Int. Cl.
*A61B 5/0225* (2006.01)
*A61B 5/022* (2006.01)

(56) References Cited

U.S. PATENT DOCUMENTS

| | | | |
|---|---|---|---|
| 6,626,840 | B2 | 9/2003 | Drzewiecki et al. |
| 8,197,416 | B1 | 6/2012 | Shankar |
| 8,708,921 | B2 * | 4/2014 | Whitt .............. A61B 5/02007 600/481 |
| 2002/0111554 | A1 | 8/2002 | Drzewiecki et al. |
| 2003/0065270 | A1 | 4/2003 | Raines et al. |
| 2004/0024324 | A1 | 2/2004 | Bratteli |
| 2004/0092832 | A1 | 5/2004 | Schnall et al. |
| 2005/0070805 | A1 | 3/2005 | Dafni |
| 2007/0021673 | A1 | 1/2007 | Arbel et al. |
| 2007/0225614 | A1 | 9/2007 | Naghavi et al. |
| 2009/0259131 | A1 | 10/2009 | Tsuji et al. |
| 2010/0298717 | A1 | 11/2010 | Parfyonov et al. |
| 2010/0305459 | A1 | 12/2010 | Whitt et al. |

OTHER PUBLICATIONS

Liu, et al., "An Oscillometry-Based Approach for Measuring Blood Flow of Brachial Arteries," ICBME 2008, Proceedings 23, pp. 481-484, Feb. 11, 2009.

"Systolic vs. Diastolic Blood Pressure Range," Vaughn's Summaries, Dec. 17, 2008. http://web.archive.org/web/20081217003248/http://www.vaughns-1-pagers.com/medicine/blood-pressure.htm.

Wang, et al., "Efficacy of fenofibrate and simvastatin on endothelial function and inflammatory markers in patients with combined hyperlipidemia: relations with baseline lipid profiles," Atherosclerosis 170 (2003), pp. 315-323.

Rastaldo, et al., "Comparison between the effects of pentobarbital or ketamine/nitrous oxide anesthesia on metabolic and endothelial components of coronary reactive hypermia," Life Sciences 69 (2001), pp. 729-738.

Philpott, et al., "Reactive Hyperemia and Cardiovascular Risk," Arteriosclerosis, Thrombosis, and Vascular Biology, 27 (2007), pp. 2065-2067.

Binggeli, et al., "Statins Enhance Postischemic Hyperemia in the Skin Circulation of Hypercholesterolemic Patients," Journal of the American College of Cardiology, vol. 42, No. 1, 2003, pp. 71-77.

Slides from Poster Presentation at the BMES Meeting (Biomedical Engineering Society Meeting); 1997.

File History of U.S. Appl. No. 12/792,504.

* cited by examiner

METHOD AND DEVICE FOR DETECTING AND ASSESSING REACTIVE HYPEREMIA USING SEGMENTAL PLETHYSMOGRAPHY

RELATED APPLICATIONS

This application is a continuation application of U.S. patent application Ser. No. 12/792,504, filed on Jun. 2, 2010, which claims the priority of U.S. Provisional Patent Application No. 61/213,369, filed on Jun. 2, 2009. The entirety of all of the aforementioned applications is incorporated herein by reference.

FIELD

The technology relates generally to medical devices and diagnosis methods and, in particular, to method and devices for measuring reactive hyperemia and endothelial dysfunction with segmental volume plethysmography and oscillometry.

BACKGROUND

Endothelial dysfunction (ED) has been shown to be of prognostic significance in predicting vascular events such as heart attack and stroke. It is the key event in the development of atherosclerosis and predates clinically evident vascular pathology by many years. ED can result from a variety of disease processes, such as hypertension, atherosclerosis, cardiovascular disease (heart disease and stroke), atrial fibrillation, congestive heart failure, peripheral vascular disease, septic shock, hypercholesterolemia, type I and II diabetes, erectile dysfunction, rheumatic arthritis, HIV, liver disease (cirrhosis, hepatitis B and C, non-alcoholic steatohepatitis, fatty liver disease), pre-eclampsia, environmental factors such as smoking, ingestion of high glycemic index carbohydrates, sedentary lifestyle and obesity. ED is also associated with states of low grade, chronic inflammation with elevated C reactive protein which leads to atherosclerosis.

ED can be improved by risk factor modification: exercise, weight loss, cessation of smoking, the use of statin drugs, beta blockade, the treatment of hypertension and hypercholesterolemia, improved diet with reduction of trans fat intake, control of diabetes. Therefore, early detection of ED may allow not only early diagnosis and treatment of ED-related diseases, but also treatment of ED itself.

Plethysmography is a non-invasive technique for measuring the amount of blood flow present or passing through, an organ or other part of the body. Segmental volume plethysmography is performed by injecting a standard volume of air into a pneumatic cuff or cuffs placed at various levels along an extremity. Volume changes in the limb segment below the cuff are translated into pulsatile pressure that are detected by a transducer and then displayed as a pressure pulse contour. Segmental volume plethysmography has been commonly used to measure blood pressure. It may also be used to check for blood clots in the arms and legs.

SUMMARY

A method for measuring reactive hyperemia in a subject is disclosed. The method includes performing a first segmental cuff plethysmography to generate a baseline arterial compliance curve and/or a baseline pressure-area (P-A) curve on a portion of the body of the subject, wherein the cuff pressure is increased to a first peak cuff pressure and immediately reduced from the first peak cuff pressure; performing a second segmental cuff plethysmography to generate a hyperemic arterial compliance curve and/or a hyperemic P-A curve, wherein the cuff pressure is increased to a second peak level, maintained at the second peak cuff pressure for a predetermined period of time, and then reduced from the second peak cuff pressure; and calculating the difference between the baseline arterial compliance curve and the hyperemic arterial compliance curve as an area between the arterial compliance curves, and/or the difference between the baseline P-A curve and the hyperemic P-A curve as an area between the P-A curve.

In one embodiment, the method further includes determining a level of endothelial dysfunction (ED) in the subject based on the result of the calculating step.

In another embodiment, the method further includes determining a risk of an ED-related disease based on the result of the calculating step.

Also disclosed is a method for determining endothelial dysfunction (ED) in a subject. The method includes: (a) inflating a cuff around a portion of the body of the subject and immediately deflating the cuff after reaching a first cuff pressure and measuring the volume and pressure changes in the cuff during the inflation process and the deflation process, (b) generating a first curve based on the measurements in step (a), (c) inflating the cuff around the portion of the body of the subject for the second time, maintaining the inflation at a second cuff pressure for a predetermined period of time, deflating the cuff, and measuring the volume and pressure changes in the cuff during the inflation process and the deflation process, (d) generating a second curve based on the measurements in step (c), (e) determining a difference between areas under the first curve and the second curve, wherein the first curve and the second curve are arterial compliance curves or pressure-area (P-A) curves; and (f) determining a level of ED or the risk of an ED-related disease based on the difference determined in step (e).

Also disclosed is a method for monitoring the efficacy of a medical procedure in a subject. The method includes performing a first measurement of reactive hyperemia in the subject using the method described above, performing a second measurement of reactive hyperemia in the subject using the method described above, and comparing the results of the first measurement and the second measurement.

In certain embodiments, wherein the medical procedure is a treatment procedure for an ED-related disease or an anesthetic procedure.

Also disclosed is an apparatus that includes: an inflatable cuff, a metering pump for inflating and deflating the cuff, a pressure transducer for measuring the pressure inside the cuff, and a computer. The computer contains means for calculating a cuff compliance curve using non-linear regression, means for calculating an arterial compliance curve and a P-A curve during the inflation and deflation process of the cuff, and means for calculating the difference between the areas under a first arterial compliance curve and a second arterial compliance curve and the difference between the areas under a first pressure-area (P-A) curve and a second P-A curve.

BRIEF DESCRIPTION OF DRAWINGS

The detailed description will refer to the following drawings, wherein like numerals refer to like elements, and wherein.

DETAILED DESCRIPTION

Described herein are methods, systems and devices for measuring arterial compliance, and generating other measurements such as arterial volumetric blood flow waveforms and pressure-area curves, over the entire transmural pressure range. These measurements can be used to measure reactive hyperemia and detect, measure and monitor various ailments such as endothelial dysfunction, other cardiovascular diseases, and pre-eclampsia as well as for monitoring the effectiveness or efficacy of anesthesia.

Embodiments include a mathematical function-calibrated cuff plethysmography. A plethysmograph is an instrument for determining and registering variations in the size of an organ or limb resulting from changes in the amount of blood present or passing through it. The calibration is achieved with a process that combines a non-linear mathematical function and the output of a metering pump. Embodiments combine concepts of segmental volume plethysmography and oscillometry to provide an actual measurement of arterial compliance over the entire transmural pressure range. Segmental volume plethysmography is a technique that is performed by injecting a standard volume of air into a pneumatic cuff or cuffs placed at various levels along an extremity. Volume changes in the limb segment underneath the cuff are translated into pulsatile pressure that are detected by a transducer and then displayed as a pressure pulse contour. Oscillometry is a process that is used to measure changes in pulsations in arteries, especially arteries of the extremities. Embodiments also generate a pressure-area curve and arterial volumetric blood flow waveforms over the entire transmural pressure range. Transmural pressure is pressure across the wall of a cardiac chamber or the wall of a blood vessel. Transmural pressure is calculated as intracavity pressure (i.e., the pressure within the cardiac chamber or blood vessel) minus extracavity pressure (i.e., the pressure outside the cardiac chamber or blood vessel).

Embodiments are used to measure reactive hyperemia and endothelial dysfunction, which is an early measure of a functional abnormality in the endothelium. The endothelium is the inner most layer of the arterial wall and is made up of a thin layer of flat endothelial cells. Endothelial dysfunction, or ED, is a well established response to cardiovascular risk factors and precedes the development of atherosclerosis (which leads to plaque development). When ED occurs, the magnitude of nitric oxide secretion is reduced and arterial vasodilation is also reduced. These changes lead to reduced reactive hyperemia that can be measured using the method and devices described herein.

ED is a predictor of overall vascular health. Accordingly, ED is an early indicator of cardiovascular disease. Indeed, ED has been shown to significantly and directly correlate to cardiovascular events such as myocardial infarction, stroke, sudden death, and heart failure. By measuring the degree of ED, embodiments described herein can be highly predictive of cardiovascular events and disease. Clinically, ED can predict the occurrence of de novo type II diabetes and the progression of metabolic syndrome to type II diabetes. ED is also associated with peripheral vascular disease and chronic renal failure, and has been shown to predict pre-eclampsia in pregnant women. Pre-eclampsia is a serious medical condition developing in late pregnancy for which there is no known cure. Pre-eclampsia is characterized by high blood pressure and proteinuria (protein in the urine). Pre-eclampsia may lead to blindness, kidney failure, liver failure, placental abruption, convulsions, and HELLP syndrome (a triad of Hemolytic anemia, Elevated Liver enzymes, Low Platelets). Pre-eclampsia occurs in as many as 10% of all pregnancies and can be fatal to both mother and child. ED has been shown to be an early warning sign for pre-eclampsia.

Additionally, interventional studies have shown a regression of ED with the treatment of risk factors through diet, exercise, weight loss, smoking cessation, diabetic management, and drugs such as statins and various lipid lowering medications. Consequently, embodiments described herein may also be used as a means to monitor progress and guide treatment and therapy in patients with ED-related diseases such as cardiovascular disease.

For example, there at two distinct populations in which measuring endothelial dysfunction (ED) is both clinically valuable and efficacious. One population consists of asymptomatic patients at risk for cardiovascular disease (CVD). The other population is patients with known CVD who are on medical therapy. In patients at risk for CVD, measuring ED can serve as an early sign of progressive heart disease. In at-risk patients taking medications for known CVD, measuring ED can also monitor progress and guide treatment.

In one embodiment, methods and devices described herein are used to monitor progress and guide treatment and therapy in patients who are taking statins. Currently, physicians prescribe statins but have no established method for measuring their effect on decreasing ED, an important component of how statin therapy works. Using reactive hyperemia as an indicator of ED, the methods and devices described herein could be used to measure the efficacy of statin drugs as well as risk factor modification (i.e., weight loss, blood sugar control, smoking cessation etc) in improving ED. These methods involve measuring the reactive hyperemia and comparing the level of hyperemia in patients at different stages of the treatment. Where the efficacy of a medical treatment, such as statin treatment, is determined, the first measurement of reactive hyperemia is preferably a measurement taken prior to the initiation of the treatment, while the subsequent measurements are taken during the course of the statin treatment. The frequency of the measurement can be determined by the medical care provider.

The medical care provider may further modify the treatment regimen based on the outcome the measurements.

The ability to measure accurate arterial flow waveforms using embodiments described herein may be beneficial in surgical, ambulatory and outpatient health care situations. Arterial flow waveform monitoring using embodiments described herein provides additional benefits beyond simple blood pressure monitoring. For example, a patient with hypovolemic shock would present the following physical manifestations in the earliest stage (referred to as the compensatory stage): increased heart rate, peripheral vasoconstriction and decreased cardiac output. An accurate arterial flow waveform measurement, such as provided by the embodiments described herein, can be obtained at any transmural pressure providing real-time, non-invasive measurement of cardiac output changes over time, in addition to constant accurate monitoring of heart rate and vascular tone.

Embodiments described herein measure ED and reactive hyperemia (an increase in the quantity of blood flow to a body part resulting from the restoration of its temporarily blocked blood flow). Embodiments make these measurements by combining oscillometry and segmental volume plethysmography fundamentals and applying non-linear equations for cuff compliance. Cuff compliance is the amount of volume change that takes place with the given pressure change of a blood pressure cuff. This relationship has demonstrated a non-linear relationship in previous studies. However, the non-linear relationship varies from cuff to cuff as well as depending on how the cuff is placed on the limb. An earlier patent, U.S. Pat. No. 6,309,359 ("the '359 patent"), which is hereby incorporated by reference, also combined oscillometry and segmental volume plethysmography fundamentals to make non-invasive determinations of peripheral arterial lumen area. However, the method and apparatus described in the '359 patent do not apply or use a non-linear, mathematical equation to generate a cuff compliance curve, instead simply using the cuff pressure that most closely corresponds to actual cuff pressure. The '359 patent method and apparatus also use different equipment, including requiring a high-frequency pump that operates at a frequency that is significantly higher than the arterial cycle frequency. Moreover, each point of data used by the '359 patent is obtained as the cuff pressure descends, as opposed to during inflation (pressure increasing) and deflation (pressure decreasing).

Figure 1:
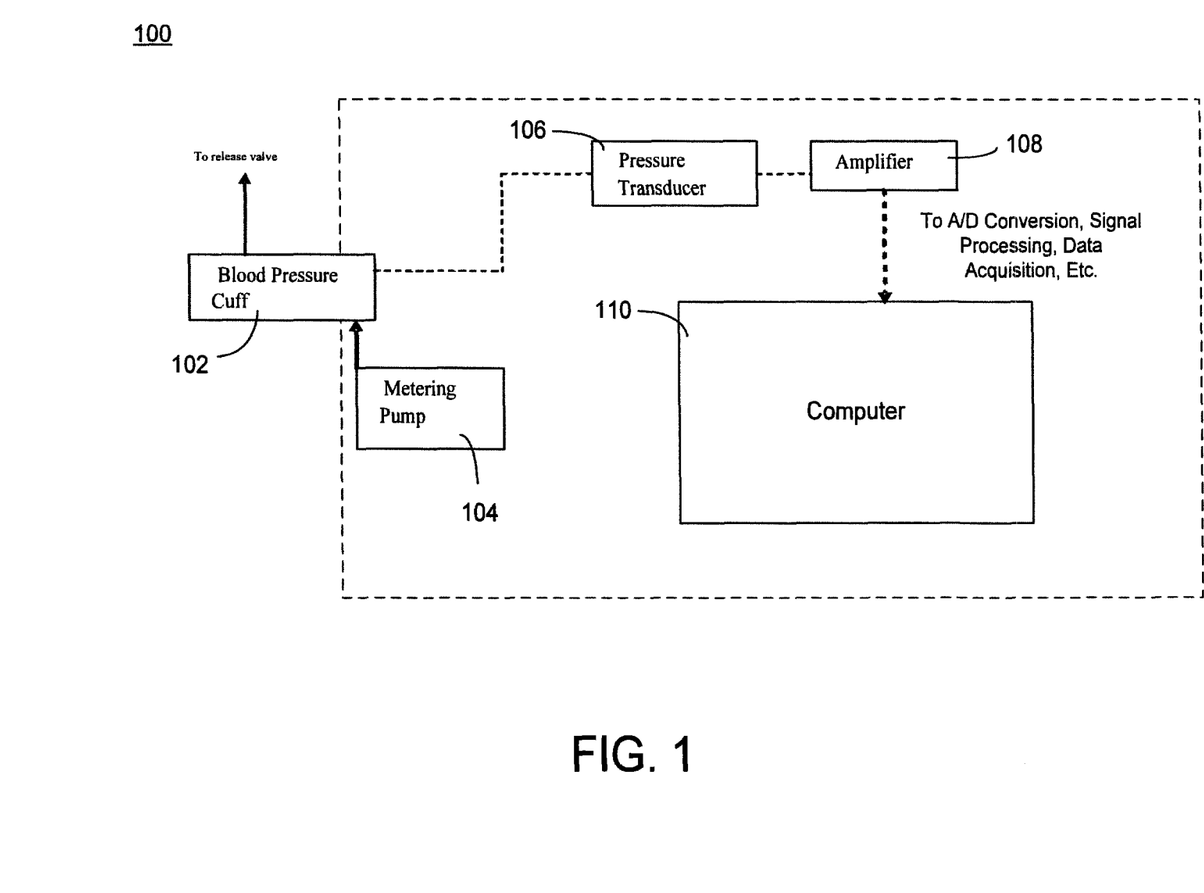
FIG. 1 is a block diagram illustrating an embodiment of a system for measuring arterial compliance, area and peripheral arterial flow.

With reference now to FIG. 1, shown is a block diagram illustrating an embodiment of a system 100 for measuring arterial compliance. System 100 includes blood pressure cuff, meter, pump and hardware and/or software necessary for data acquisition described herein. Embodiment of system 100 includes a blood pressure cuff 102, metering pump 104, pressure transducer 106, amplifier 108 and computer 110. Blood pressure cuff 102 may be a standard blood pressure cuff 102 traditionally inflated to apply pressure to a limb so that blood pressure may be measured. The blood pressure cuff 102 is typically placed around the upper arm of the patient. However, the device could be used when placed around any portion of a limb for adults, children, or animals. Blood pressure cuff 102 size may be configured for the intended use in each case. Metering pump 104 includes a pump used to inflate blood pressure cuff 102 with a volume of air and a meter to measure inflation level of cuff (volume of air (e.g., in liters/minute) injected into the cuff 102). In one embodiment, the pump 104 is a low frequency pump. Pressure transducer 106 detects pulsatile pressure in the arteries of the limb by measuring the pressure in the cuff. The pressure transducer 106 generates a signal, indicative of the pulsatile pressure that is input into the amplifier 108. Amplifier 108 amplifies the pulsatile pressure signal and inputs the amplified signal into the computer 110.

The computer 110 may perform analog to digital (A/D) conversion of the amplified signal, as necessary, process the signal to acquire the necessary data, perform the methods, including calculating and applying the mathematical equations and generating the various curves, graphs and other displays, described herein. The computer 110 may be a general purpose computer with a processor(s) and memory that stores instructions (e.g., as one or more computer programs) to perform these functions, or a special purpose computer so programmed. Accordingly, the software included on the computer 110 may include one or more data acquisition and mathematical programs and is capable of developing the non-linear mathematical functions used in the method, performing band-pass filtering and other filtering and signal processing as necessary, and performing mathematical transformations, e.g., for area measurement under curves and numerical integration of arterial compliance curves for the development of pressure-area curves. Alternatively, instead of or in addition to computer 110, system 100 may include circuitry to perform some of these functions, include a separate A/D converter, a band-pass filter and other specialized circuitry.

Components of the system 100, such as the metering pump 104, pressure transducer 106, amplifier 108 and computer 110 may be housed within a single housing, as indicated by dashed lines in FIG. 1, connected to the blood pressure cuff 102.

Figure 3:
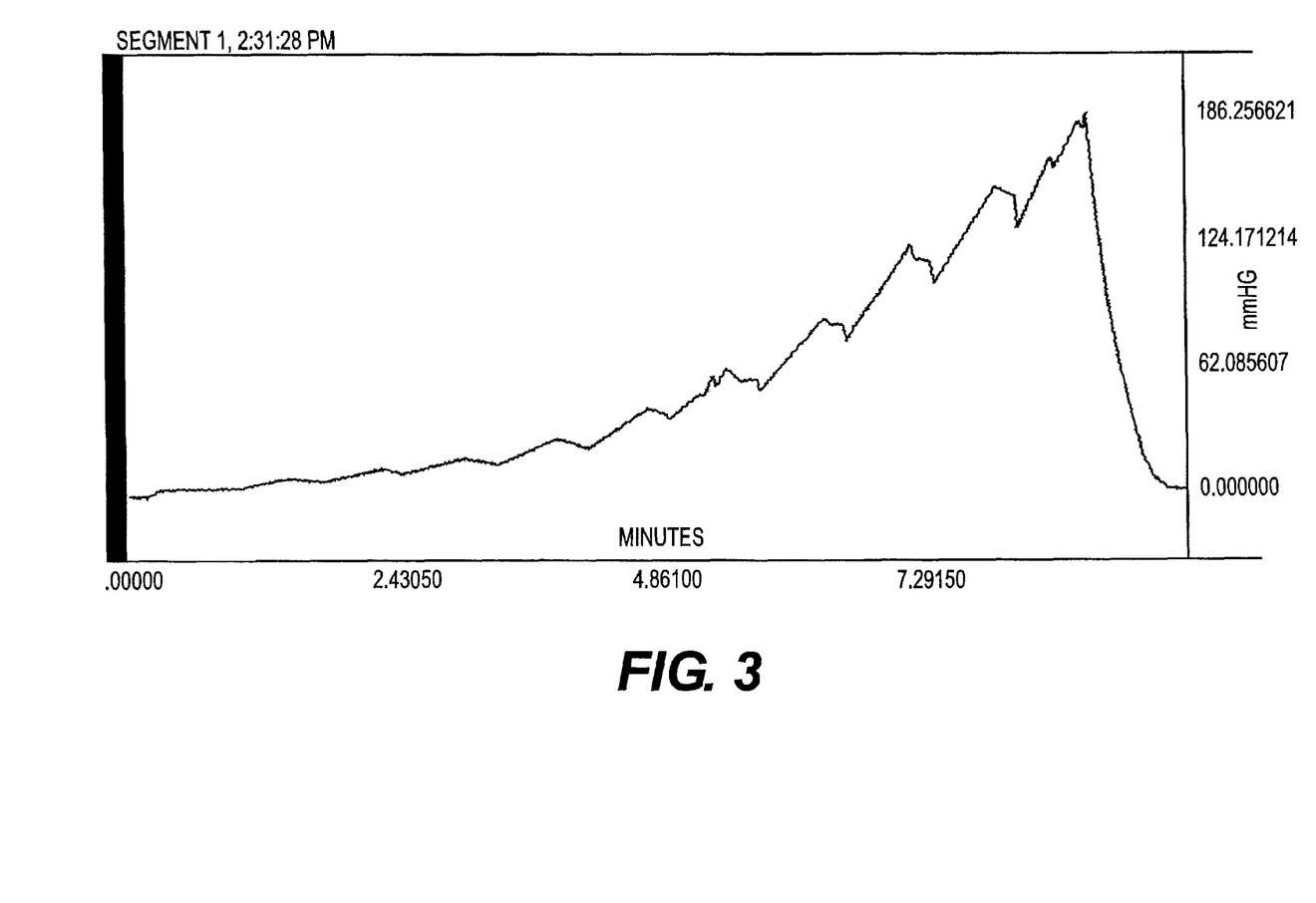
FIG. 3 is a graph illustrating data acquired using an embodiment of the system and method for measuring arterial compliance, area and peripheral arterial flow.

Embodiments of the method described herein obtain/acquire data during both inflation and deflation of the blood pressure cuff 102. In embodiments, a known volume of air is injected into the blood pressure cuff 102 at each increment from 0 mm Hg to a pressure significantly higher than the patient's systolic blood pressure (i.e., pressure that corresponds to the pressure in the arteries as the heart contracts and pumps blood into the arteries), yet not too uncomfortable for the patient (e.g., approximately 180 mm Hg). Each pressure change (dP) is measured for each known volume change (dV) along the entire pressure ascent. FIG. 3 is a chart of data acquired during the inflation process In some embodiments, the above-described data (measured pressure change for each known volume change) obtained during the inflation is used to develop $(dV/dP)_{cuff}$ versus average cuff pressure curve (referred to as "the average cuff pressure curve"), where dV is change in volume, dP is change in pressure and $(dV/dP)_{cuff}$ is cuff compliance, which changes non-linearly with cuff pressure.

The data obtained above is plotted on the average cuff pressure curve. A non-linear regression is performed on this data, developing an equation where $(dV/dP)_{cuff}$ can be obtained at any cuff pressure. In one embodiment, the non-linear regression is performed using inverse polynomial second order functions. Successful coefficients of determination have been developed using such functions.

In other embodiments, during deflation of the blood pressure cuff (the descent portion of the average cuff pressure curve), various additional data is obtained and additional functions are performed. In one embodiment, band pass filtering method (i.e., band pass filtering at various frequencies filters out other data so as to determine desired pressure data) may be used to obtain systolic blood pressure, diastolic blood pressure, and mean arterial blood pressure (i.e., the average blood pressure during a single cardiac cycle (i.e., over one cycle of a given arterial pressure waveform)) via oscillometry. In another embodiment, band pass filtering is used to provide the magnitude of pressure pulses that take place at each cuff pressure $(dP)_{artery}$.

Arterial compliance $(dV/dP)_{artery}$, which provides the measure of arterial smooth muscle activity and resulting endothelial dysfunction) at any transmural pressure can then be obtained via the following equation:

Arterial Compliance Calculation at Any Transmural Pressure $$\left(\frac{dV}{dP}\right)_{artery} = \frac{(dP)_{artery} \times \left(\frac{dV}{dP}\right)_{cuff}}{[\text{Systolic} - \text{Diastolic}]}. \qquad \text{Equation 1}$$

A curve is generated using Equation 1. The integration of the curve obtained from Equation 1 results in a pressure-area (P-A) curve. (Note: all volume measurements can be converted to area measurements if volume is divided by effective cuff length). All compliance measurements can be normalized by using Equation 2 below, where all volume measurements can be converted to area by once again dividing by effective cuff length.

Normalized Arterial Compliance Equation $$C = \frac{\left(\frac{dV}{dP}\right)_{artery}}{V_0}. \qquad \text{Equation 2}$$

$V_0$ is base volume of patient. By dividing the arterial compliance by the patient base volume, the arterial compliance is normalized. The process described above may be used to perform a variety of measurements.

In one embodiment, the process is used for the development of an accurate arterial flow waveform by obtaining values for $(dV/dP)_{artery}$ at any transmural pressure, taking derivative of the original pressure descent waveform to obtain a waveform that is $(dP/dt)_{artery}$, and multiplying $(dP/dt)_{artery}$ by $(dV/dP)_{artery}$ to obtain an accurate flow waveform. The result is an accurate arterial flow waveform $(dV/dt)_{artery}$.

In another embodiment, the process is used for the measurement of endothelial dysfunction by obtaining a baseline arterial compliance curve and pressure-area curve as discussed above, holding the blood pressure cuff above a patient's systolic pressure for a given period of time (inducing hyperemia), obtain a second (i.e., hyperemic) compliance curve and pressure-area curve, and calculating the difference between the baseline curve and the hyperemic curve. The difference between the two curves represents the degree of endothelial dysfunction.

Figure 2:
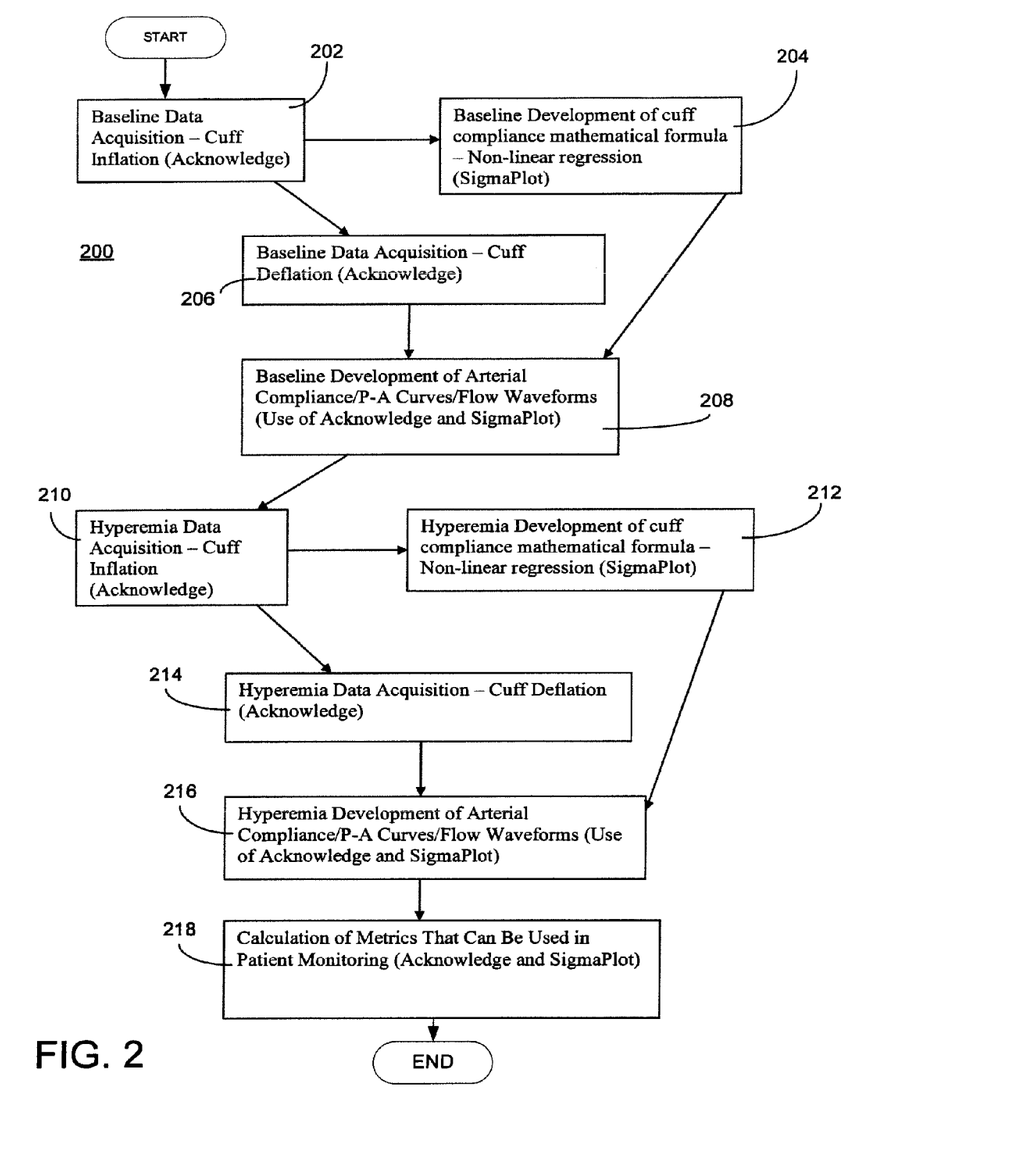
FIG. 2 is a flow chart illustrating an embodiment of a method for measuring arterial compliance, area and peripheral arterial flow.

With reference now to FIG. 2, shown is a flowchart illustrating a method 200 for measuring arterial compliance. Baseline data is acquired during cuff inflation, block 202. See FIG. 3 for a graph of baseline data acquired during cuff inflation. The baseline data acquisition 202 may include using the metering pump 104 and pressure transducer 106 during cuff 102 inflation to measure air volume injection into the pump and cuff pressure, respectively. The baseline data acquisition 202 may further include placing the cuff 102 about a peripheral limb of a patient or subject and starting the cuff at 0 mm Hg. A known volume of air may be injected into the cuff 102 while recording cuff pressure change. The baseline data acquisition 202 may be accomplished, e.g., using data acquisition software program running on computer 110. The data acquisition program may receive input from pressure transducer 106 and/or metering pump 104 (e.g., that has been converted to digital via A/D converter and/or otherwise signal processed). A variety of data acquisition programs may be used, such as, for example, Acknowledge™. The baseline data acquisition 202 obtains the cuff compliance at given average cuff pressure, where average cuff pressure equals the cuff pressure after a known volume of air injection plus the cuff pressure before the known volume of air injection, divided by two (2). As described above, the volumetric inflation of the cuff is continued up to a pressure significantly higher than the subject systolic pressure yet not too uncomfortable for the subject (e.g., approximately 180 mm Hg).

Baseline cuff compliance equation/formula is generated, block 204. As indicated above, this may be achieved using non-linear regression. In embodiments, the baseline cuff compliance formula generation can begin as soon as cuff inflation has been completed. A mathematical equation representing cuff compliance may be developed by (i) plotting average cuff pressure (x) versus cuff compliance (y) and performing a non-linear regression as stated above. The baseline cuff compliance equation/formula may be generated 204 using a mathematical software program running on computer 110. The mathematical program may receive input from the data acquisition program and may perform, e.g., non-linear regression using, e.g., an inverse polynomial second order function(s). A variety of data acquisition programs may be used, such as, for example, SigmaPlot™.

With continued reference to FIG. 2, additional baseline data is acquired during cuff deflation as described above, block 206. Additional baseline data acquisition 206 may be performed, e.g., using data acquisition program. After this additional baseline data acquisition 206 is performed, band-pass filtering and development of arterial compliance curves, P-A curves and arterial flow waveforms are performed, block 208.

To develop baseline curves and waveforms, the pressure in the cuff is immediately released after the cuff pressure has gone above the patient systolic pressure and the measurements described above are taken. In other words, cuff pressure is raised so that it is above the patient systolic pressure and then immediately released. To develop reactive hyperemia curves and waveforms (see below), the cuff pressure is held for a period of time sufficient to trigger an endothelial reaction and the measurements described above are taken. In embodiments described herein, the period of time is the time that is necessary to achieve total relaxation of the patient's smooth muscle tissue. Relaxation of the smooth muscle tissue is typically necessary to achieve accurate reactive hyperemic measurements. In one embodiment, the cuff pressure is held for a period of 1-10 minutes. In another embodiment, the cuff pressure is held for a period of 2-5 minutes. In yet another embodiment, the cuff pressure is held for about 5 minutes. The longer the cuff pressure can be held, the more assured the tester will be that the patient's smooth muscles have been relaxed and accurate reactive hyperemic measurements will be taken. The usual limiter on holding the cuff pressure is patient comfort; the longer the cuff pressure is held the more uncomfortable and, eventually, painful the procedure becomes. Elderly, ill or weakened patients tend to be able to withstand less time than younger, healthy patients.

After the baseline data has been generated, as described above, hyperemia data may be generated by basically repeating the above steps after a brief period of patient hyperemia. Hyperemia data is acquired during inflation of the cuff, block 210. The hyperemia data may be acquired by again starting the cuff at 0 mm Hg and inflating the cuff as described above. Acquisition 210 may include using the metering pump 104 and pressure transducer 106 during cuff 102 inflation to measure air volume injection into the pump and cuff pressure, respectively. Again, a known volume of air may be injected into the cuff 102 while recording cuff pressure change.

With continuing reference to FIG. 2, hyperemia cuff compliance mathematical equation is generated, block 212. Again, the hyperemia cuff compliance mathematical equation may be generated as described above. Additional hyperemia data is acquired during cuff deflation, block 214. After this additional data is acquired, band-pass filtering and development of arterial compliance curves, P-A curves and arterial flow waveforms for hyperemia are performed, block 216. Metrics to detect conditions or monitor the patient are calculated, block 218. The metrics may include, e.g., (a) comparing various curves of baseline data and hyperemic data, (b) calculating the differences between the curves as an area between the curves, and, e.g., (c) determining a level of ED (or, e.g., the presence of pre-eclampsia or other diseases, etc.) based on the calculated area. For example, such metrics may provide outputs indicating, for example, the presence of ED.

In one embodiment, the change between arterial compliance normal (baseline) curve, generated in 208, and the arterial compliance hyperemia curve, generated in 216, is calculated at a given transmural pressure.

In another embodiment, the change between arterial compliance normal (baseline) curve, generated in 208, and the arterial compliance hyperemia curve, generated in 216, can be calculated across a range of transmural pressures.

In another embodiment, the change between P-A normal (baseline) curve, generated in 208, and the P-A reactive hyperemia curve, generated at 216, is calculated at a given transmural pressure.

In another embodiment, the change between P-A normal (baseline) curve, generated in 208, and the P-A reactive hyperemia curve, generated at 216, is calculated across a range of transmural pressures.

In another embodiment, arterial flow waveforms (at any given transmural pressure or range of transmural pressures) for normal (baseline) curves and/or reactive hyperemia curves are calculated and compared.

In another embodiment, average flow waveforms (at any given transmural pressure or range of transmural pressures) for normal (baseline) curves and/or reactive hyperemia curves are calculated and compared.

In another embodiment, the computer 110 contains means for calculating an arterial compliance curve and a P-A curve during the inflation and deflation process of the cuff, means for calculating difference between areas under a first arterial compliance curve and a second arterial compliance curve and difference between areas under a first pressure-area (P-A) curve and a second P-A curve, and means for band pass filtering data.

Many of these metrics are significant in that they have never been performed over a range of transmural pressures. Other devices that perform similar metrics only do so for single points of data. Conducting these metrics over a range of transmural pressures allows more data to be compared and more information gathered from the results. The above metrics enable results to be compared over a range of pressures. More importantly, comparing the above curves of data enables the differences between the curves to be calculated as an area (see FIGS. 7-8). The lesser the area between the curves, the higher degree of ED; in other words, there is an inverse relationship between the area and the amount of ED. In certain embodiments, a scoring system is developed in which certain amounts of area (e.g., a range of area), calculated from the differences between the curves, correspond to certain levels of ED.

With reference to FIG. 3, shown is a graph of sample data acquisition during cuff inflation and deflation. The graph shows cuff pressure over time. By noting the time, the change in cuff pressure over a given time can be determined and compared to the change of cuff injection volume (not shown here) over the same time. Using this data, cuff compliance and average cuff pressure can be calculated.

Figure 4:
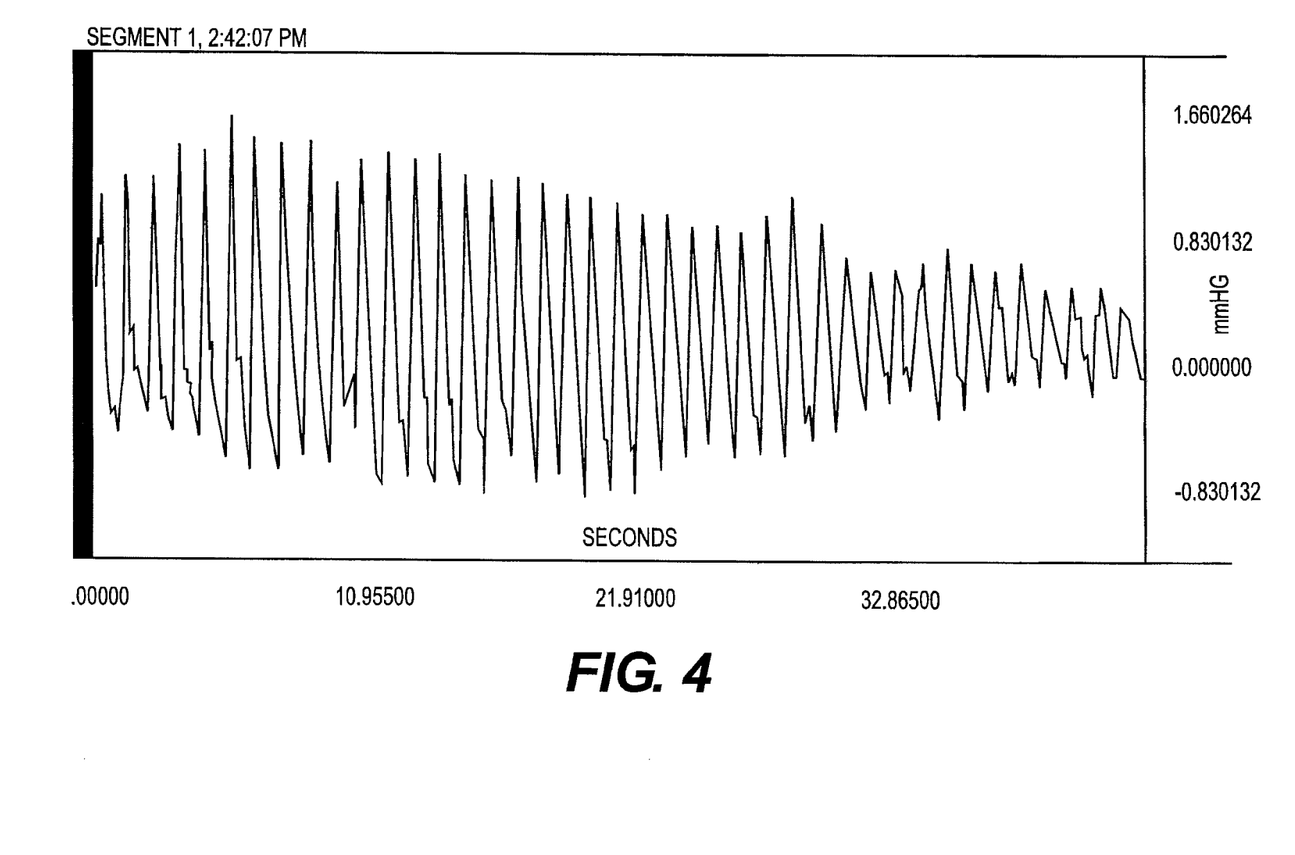
FIG. 4 is a graph illustrating data acquired and filtered using an embodiment of the system and method for measuring arterial compliance, area and peripheral arterial flow.

With reference to FIG. 4, shown is a graph of sample data obtained during descent (deflation of cuff) that has been band pass filtered to provide arterial pressure pulses. The band pass filtering removes other pressure data received from the pressure transducer to leave only, in this example, the arterial pressure pulse data. In this example, the band pass filtering may be performed at 0.5 to 5.0 Hertz.

Figure 5:
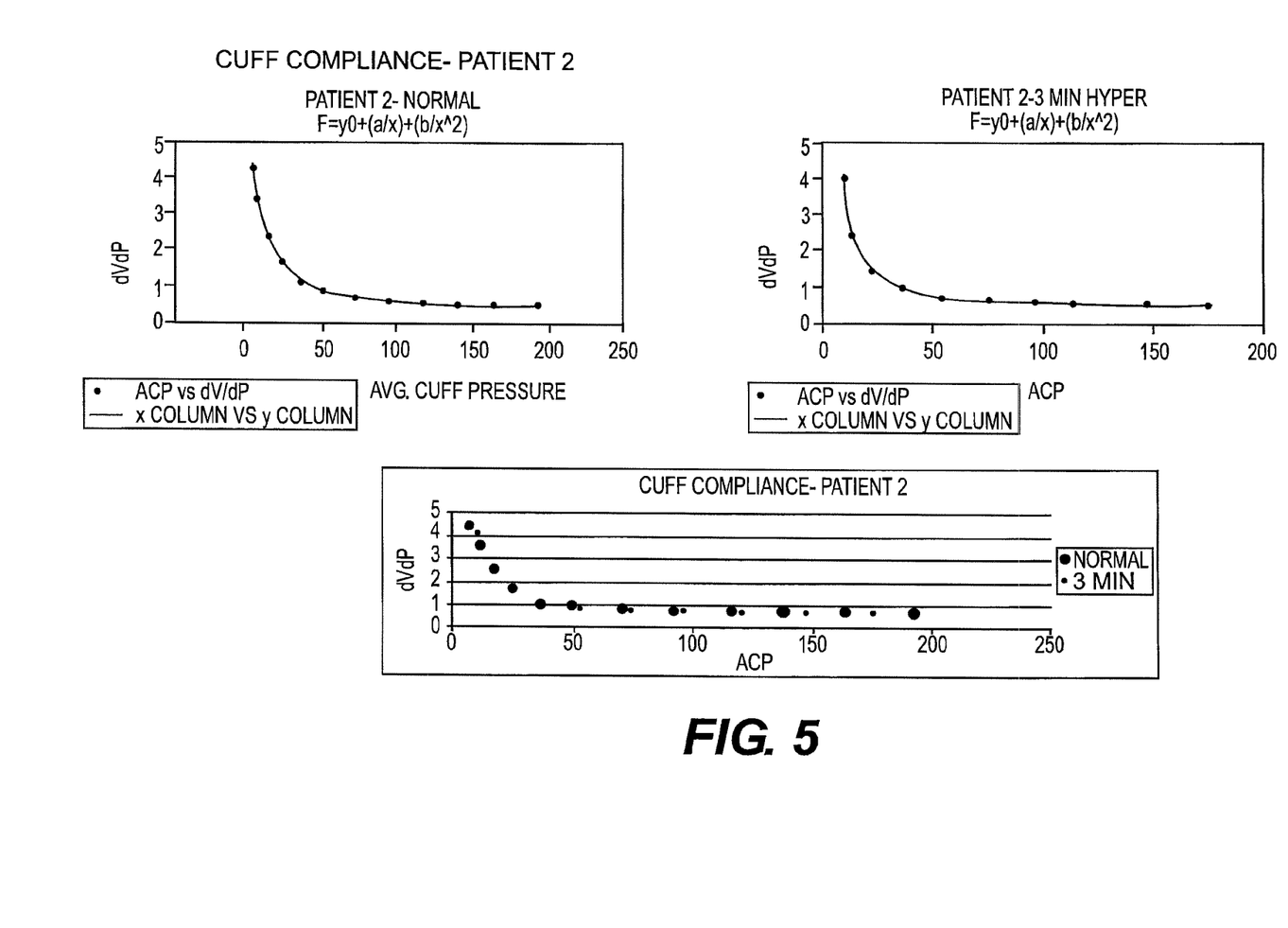
FIG. 5 includes graphs illustrating cuff compliance calculated using an embodiment of the system and method for measuring arterial compliance, area and peripheral arterial flow.

With reference to FIG. 5, shown are example cuff compliance curves generated during pressure ascent (inflation of the cuff). The cuff compliance curves may be generated as described above.

Figure 6:
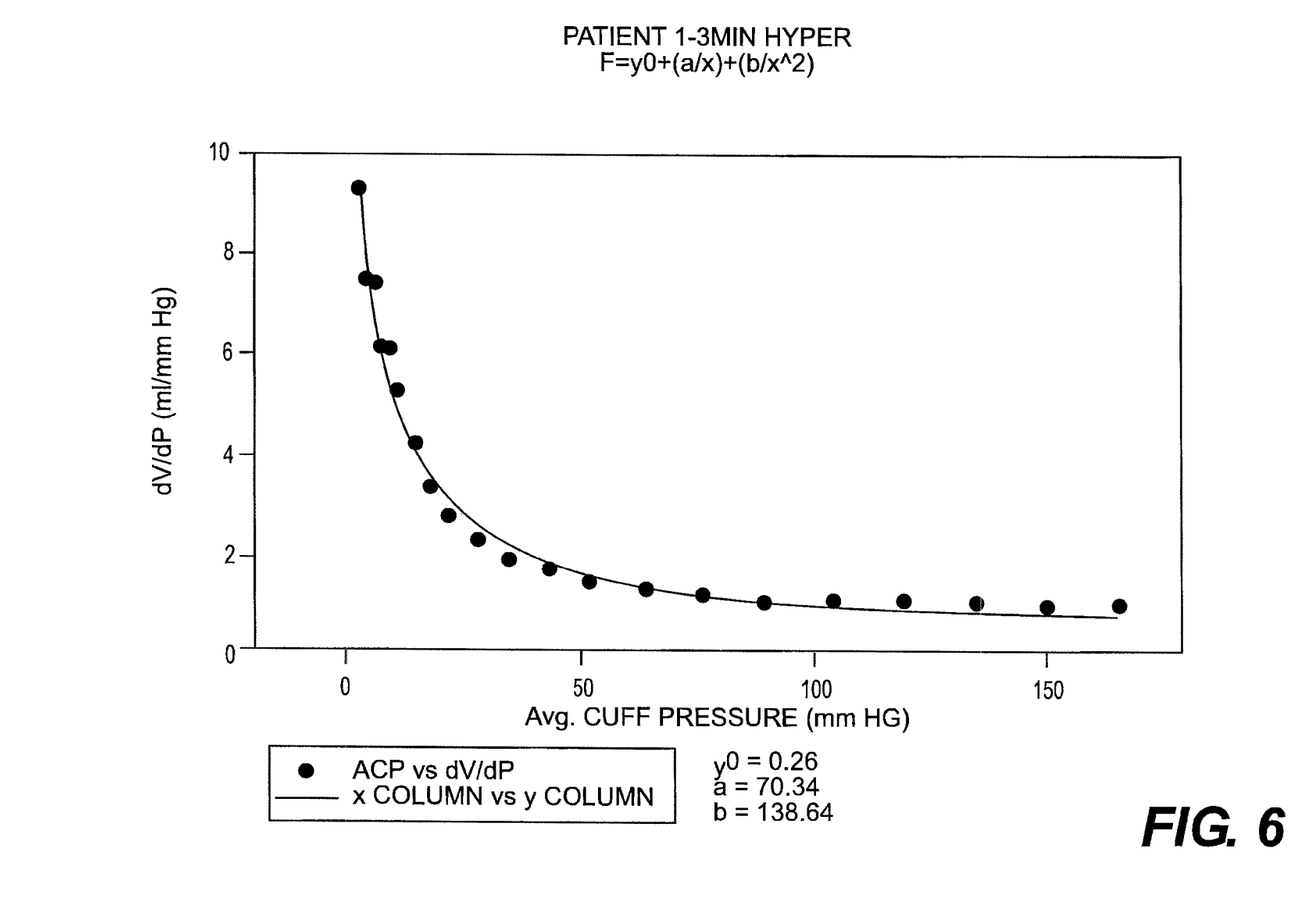
FIG. 6 is a graph illustrating cuff compliance calculated using an embodiment of the system and method for measuring arterial compliance, area and peripheral arterial flow.

With reference to FIG. 6, shown is an example cuff compliance curve generated during pressure ascent using coefficients generated using non-linear regression described above. For example, inverse polynomial second order functions may be used.

The following is sample equation output where non-linear equation for cuff compliance was developed as described above. Specifically, the information below is a sample output from a non-linear regression (using an inverse polynomial second order function) performed to develop the cuff compliance curve.

Sample Output from Non-Linear
Regression Used to Develop Cuff Compliance Curve
Nonlinear Regression
Equation: Polynomial, Inverse Second Order
$f = y0 + (a/x) + (b/x^2)$

| R | Rsqr | Adj Rsqr | Standard Error of Estimate | |
|---|---|---|---|---|
| 0.9947 | 0.9895 | 0.9883 | 0.2858 | |
| | Coefficient | Std. Error | t | P | VIF |
| y0 | 0.2598 | 0.1091 | 2.3811 | 0.0285 | 3.0614 |
| a | 70.3371 | 3.3041 | 21.2880 | <0.0001 | 17.8907< |
| b | −138.6316 | 15.6635 | −8.8506 | <0.0001 | 12.2896< |

Analysis of Variance:

Uncorrected for the mean of the observations:

| | DF | SS | MS |
|---|---|---|---|
| Regression | 3 | 349.7290 | 116.5763 |
| Residual | 18 | 1.4705 | 0.0817 |
| Total | 21 | 351.1995 | 16.7238 |

Corrected for the mean of the observations:

| | DF | SS | MS | F | P |
|---|---|---|---|---|---|
| Regression | 2 | 138.7197 | 69.3598 | 849.0321 | <0.0001 |
| Residual | 18 | 1.4705 | 0.0817 | | |
| Total | 20 | 140.1902 | 7.0095 | | |

Figure 7:
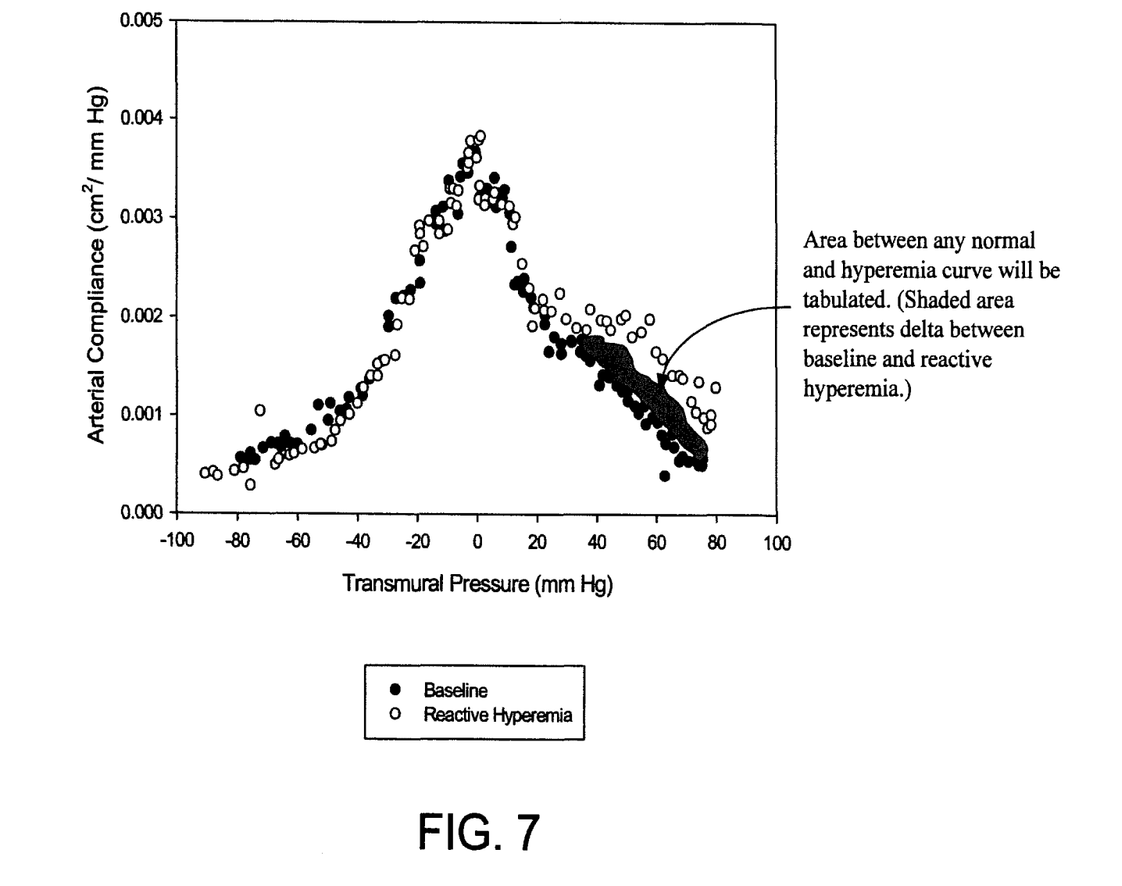
FIG. 7 is a graph illustrating a metric applied using an embodiment of the system and method for measuring arterial compliance, area and peripheral arterial flow.
Figure 8:
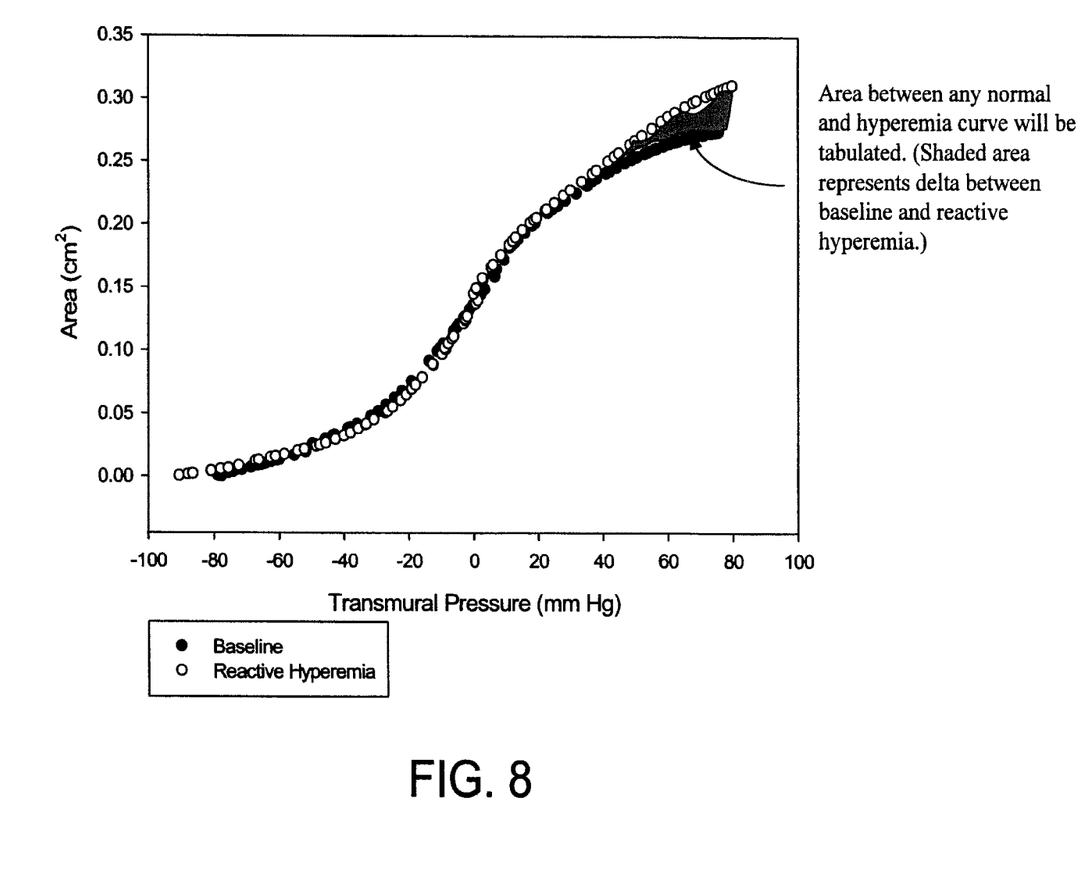
FIG. 8 is a graph illustrating a metric applied using an embodiment of the system and method for measuring arterial area.

The resulting arterial compliance versus transmural pressure curves (arterial compliance curve) are shown in FIGS. 7 and 8. The differential between normal area measurements and hyperemia measurements provides a quantitative measure of endothelial dysfunction. For example, FIG. 7 is a graph illustrating baseline and hyperemia arterial compliance curves. The differential/change between the two curves is indicated by the shaded area, which indicates the presence of endothelial dysfunction. The size of this shaded area is inversely proportional to the magnitude of endothelial dysfunction or the risk/presence of ED-related diseases (e.g., the risk/presence of pre-eclampsia).

In one embodiment, a differential percentage (i.e., the area between the baseline arterial compliance curve and the hyperemia arterial compliance curve divided by the area under the baseline arterial compliance curve) of 10% or less indicates ED or the risk/presence of an ED-related disease. In another embodiment, a differential percentage less than 7% indicates ED or the risk/presence of an ED-related disease. In another embodiment, differential percentage less than 4.5% indicates ED or the risk/presence of an ED-related disease. In summary, the lesser differential area between the baseline arterial compliance curve and the hyperemia arterial compliance curve, the greater the indication of ED or the risk/presence of an ED-related disease. In other embodiments, different thresholds are given to patient populations of different age, sex, race or geological location In other embodiment, a scoring chart for ED based on this area, are developed in which different levels of ED correspond to different sizes of the shaded area.

In a preferred embodiment, the differential in the arterial compliance curves is determined in the portion from zero transmural pressure to the maximum transmural pressure.

In certain embodiment, a single point from a patient's normal (baseline) arterial compliance curve is compared to a single point from the patient's hyperemic arterial compliance curve at the same transmural pressure value. In a preferred embodiment, the single point comparison of the arterial compliance curves is made in the portion from zero transmural pressure to the maximum transmural pressure.

Likewise, FIG. 8 is a graph illustrating baseline and hyperemia P-A curves. The differential/change between the two curves is indicated by the shaded area, which is inversely proportional to the presence of endothelial dysfunction. The area of this shaded area is inversely proportional to the magnitude of endothelial dysfunction or other disease (e.g., the presence of pre-eclampsia). In one embodiment, a differential percentage (i.e., the area between the baseline P-A curve and the hyperemia P-A curve divided by the area under the baseline P-A curve) of 10% or less indicates ED or the risk/presence of an ED-related disease. In another embodiment, a differential percentage less than 7% indicates ED or the risk/presence of an ED-related disease. In another embodiment, differential percentage less than 4.5% indicates ED or the risk/presence of an ED-related disease. In summary, the lesser differential area between the baseline P-A curve and the hyperemia P-A curve, the greater the indication of ED or the risk/presence of an ED-related disease. In other embodiment, different thresholds are given to patient populations of different age, sex, race or geological location In other embodiment, a scoring chart for ED based on this area, are developed in which different levels of ED correspond to different sizes of the shaded area.

In a preferred embodiment, the differential in the P-A curves is determined in the portion from zero transmural pressure to the maximum transmural pressure.

In certain embodiment, a single point from a patient's normal (baseline) P-A curve is compared to a single point from the patient's hyperemic P-A curve at the same transmural pressure value. In a preferred embodiment, the single point comparison of the arterial compliance curves is made in the portion from zero transmural pressure to the maximum transmural pressure.

In another embodiments, the actual flow waveform at any given transmural pressure is calculated. The actual flow waveform may be calculated at any transmural pressure where blood flow is permitted by cuff pressure.

In other embodiments, the level of ED is used as an indicator for a diseased condition or as an indicator for the risk of a diseased condition. Such diseased conditions include, but are not limited to, pre-eclampsia, hypertension, atherosclerosis, cardiovascular disease (including coronary artery disease and stroke), atrial fibrillation, congestive heart failure, peripheral vascular disease, septic shock, hypercholesterolemia, type I and II diabetes, erectile dysfunction, rheumatic arthritis, HIV, and liver disease (cirrhosis, hepatitis B and C, non-alcoholic steatohepatitis, fatty liver disease).

In other embodiments, the pressure/volume measurements taken during the segment cuff plethysmography are used for purposes other than measuring ED. For example, the pressure/volume measurements can be used to monitor cardiac function by taking the derivative of pressure waveform and mathematically superimposing all points with the nonlinear cuff compliance relationship to generate a calibrated flow waveform.

The embodiments described herein enable a physician, for example, to both measure and monitor reactive hyperemia, ED, ED-related diseases, cardiovascular conditions and the efficacy of various forms of treatment. Key metrics obtained include actual measurements of peripheral arterial flow, arterial compliance, and arterial area across the entire arterial transmural pressure range.

A significant benefit of the embodiments described herein is the early diagnosis of ED-related diseases. A physician, for example, is able to gain valuable information from the reactive hyperemic measurement. Device embodiments provide benefits to clinicians in providing a simple method to diagnose patients that are currently classified as asymptomatic, as well as quantify the efficacy of current and novel treatments in patients already diagnosed with disease. Another significant benefit of the embodiments described herein is the ability to monitor the effectiveness of treatments for ED.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A system for measuring arterial blood flow in a subject, comprising:
   an inflatable cuff;
   a low-frequency metering pump for inflating the cuff, wherein the metering pump operates at a frequency that is not higher than arterial cycle frequency of the subject;
   a pressure transducer for measuring pressure inside the cuff; and a computer configured to:
  generate a pressure descent curve and a cuff compliance curve by directly measuring volume change in said cuff with said metering pump and pressure change inside the cuff with said pressure transducer;
  generate an arterial compliance $(dV/dP)_{artery}$ curve during inflation and deflation processes of the cuff that allows determination of $(dV/dP)_{artery}$ values at any transmural pressure;
  calculate a derivative of said pressure descent curve to obtain a $(dP/dt)_{artery}$ curve; and
  multiply $(dP/dt)_{artery}$ by $(dV/dP)_{artery}$ to obtain an arterial flow $(dV/dt)_{artery}$ curve.

2. The apparatus of claim 1, further comprising an amplifier.

3. The apparatus of claim 2, further comprising means for band pass filtering data.

4. A method for measuring arterial blood flow in a subject, comprising:
  performing a first segmental cuff plethysmography on a portion of the body of the subject with the system of claim 1, wherein said performing comprises:
  increasing cuff pressure in the inflatable cuff to a peak cuff pressure and immediately reducing cuff pressure in the inflatable cuff from the peak cuff pressure;
  generating, with the computer, a pressure descent curve based on change in cuff pressure and cuff volume;
  generating, with the computer, an arterial compliance $(dV/dP)_{artery}$ curve that allows determination of $(dV/dP)_{artery}$ values at any transmural pressure;
  calculating, with the computer, a derivative of said pressure descent curve to obtain a $(dP/dt)_{artery}$ curve; and
  multiplying, with the computer $(dP/dt)_{artery}$ by $(dV/dP)_{artery}$ to obtain an arterial flow curve $(dV/dt)_{artery}$.

5. The method of claim 4, wherein a cuff compliance curve is generated using the metering pump to measure the volume change in the cuff and the pressure transducer to measure pressure change for each known volume change.

6. The method of claim 4, wherein the peak cuff pressure is in the range of 150-180 mmHg.

7. The method of claim 4, wherein the arterial compliance $(dV/dP)_{artery}$ is obtained via the following equation:

$$(dV/dP)_{artery} = (dP)_{artery} \times (dV/dP)_{cuff}$$

$$[P_{sys} - P_{dia}]$$

wherein $(dP)_{artery}$ is the magnitude of pressure pulses that take place at each cuff pressure, $P_{sys}$ is systolic blood pressure, and $P_{dia}$ is diastolic blood pressure.

8. The method of claim 7, wherein a band pass filtering method is used on the pressure descent curve to obtain $P_{sys}$ and $P_{dia}$.

* * * * *